United States Patent [19]

Reinert et al.

[11] 4,334,881
[45] Jun. 15, 1982

[54] METHOD AND APPARATUS FOR AUTOMATIC END-POINT DETECTION IN TRIPOLYPHOSPHATE SEQUESTRATION OF HARDNESS

[75] Inventors: Raymond L. Reinert, Louisville; Charles D. Kaufman, Crestwood, both of Ky.

[73] Assignee: General Electric Company, Louisville, Ky.

[21] Appl. No.: 223,661

[22] Filed: Jan. 9, 1981

[51] Int. Cl.$^3$ .......................... G01N 33/18; B08B 3/10
[52] U.S. Cl. .................................... 23/230 A; 422/62; 422/76; 134/18; 134/29; 134/56 D
[58] Field of Search .......................... 23/230 A, 230 R; 422/75, 76, 62; 134/18, 29, 57 D, 56 D, 58 D; 364/497; 204/1 T, 195 T

[56] References Cited

U.S. PATENT DOCUMENTS

| | | | |
|---|---|---|---|
| 2,928,774 | 3/1960 | Leisey | 204/1 |
| 3,298,934 | 1/1967 | Angeleri | 204/1 |
| 3,308,041 | 3/1967 | Strickler | 204/1 |
| 3,368,969 | 2/1968 | Palen . | |
| 3,383,310 | 5/1968 | Ammer | 422/75 X |
| 3,490,467 | 1/1970 | Gore et al. | 134/18 |
| 3,697,224 | 10/1972 | Means | 23/230 R |
| 3,895,913 | 7/1975 | Bockowski et al. | 23/230 R |
| 3,896,827 | 7/1975 | Robinson | 134/18 X |
| 4,180,440 | 12/1979 | Gibboney et al. | 422/75 X |

OTHER PUBLICATIONS

Niven, Jr., Wm. W., "Industrial Detergency", pp. 230-232, Reinhold Pub., (1955).
Vance, Robert F., J. Am. Oil Chem. Soc., 46, 639-641, (1969).

Primary Examiner—Ronald E. Serwin
Attorney, Agent, or Firm—H. Neil Houser; Radford M. Reams

[57] ABSTRACT

A method and apparatus for automatic end-point detection in tripolyphosphate sequestration of hardness are disclosed. A desired approximate 1:1 molar ratio of the hardness elements calcium (Ca) and magnesium (Mg) to sodium tripolyphosphate in a wash water solution is achieved by adding to the wash water solution sodium tripolyphosphate at a preselected rate as the electrical conductivity of the wash water solution is monitored. The desired approximate 1:1 molar ratio of hardness element to sodium tripolyphosphate is obtained, irrespective of variations of concentration levels of hardness elements in the wash water solution or in the soils being removed by the solution, either (a) by detecting the maximum rate of change of conductivity of the wash water solution and terminating the addition of sodium tripolyphosphate when the maximum rate of change of conductivity of the wash water solution is detected or (b) when the pH of the wash solution is to be above 11; by detecting the 5:2 molar ratio of calcium hardness to tripolyphosphate by determining when the conductivity of the wash water solution first increases substantially; then adding 1.5 times more sodium tripolyphosphate than had been added when conductivity increased substantially to chelate the calcium hardness; and raising the pH to at least 11 to precipitate the magnesium hardness. Apparatus is disclosed for implementing automatically the sequestration method of the present invention in, for example, the home dishwasher environment.

24 Claims, 7 Drawing Figures

METHOD AND APPARATUS FOR AUTOMATIC END-POINT DETECTION IN TRIPOLYPHOSPHATE SEQUESTRATION OF HARDNESS

BACKGROUND OF THE INVENTION

The method and apparatus of the present invention relate generally to water softening sequestration and, more particularly, to automatic end-point detection in sodium tripolyphosphate sequestration of hardness elements of a wash water solution irrespective of variations of concentration levels of hardness elements in the wash water solution or in the soils being removed by the wash water solution.

It is well known that the hardness elements in a wash water solution affect detrimentally the level of satisfactory detergent cleaning of objects being washed. The hardness of water is principally due to its calcium (Ca) and magnesium (Mg) content. Hereinafter, such total water hardness is expressed in terms of an equivalent amount of calcium carbonate ($CaCO_3$).

When detergent is added to the wash water solution, the Ca and Mg ions in the wash water solution tend to react with various ions present in the detergent. These reactions may result in the precipitation of essentially insoluble Ca and Mg compounds, which results in loss of detergent values. Thus, the hardness elements in the wash water solution must be dealt with in some fashion in order to obtain the desired cleaning level using a reasonable detergent level.

Sequestration is the preferred embodiment for achieving in situ softening of hard water in washing processes. In the sequestration method, a metal complexing agent is added to the wash water solution, and the agent chelates the hardness ions to form soluble chelate salts. These chelate salts are stable and prevent the formation of insoluble compounds that might otherwise form. It is well known that the ideal concentration level of the sequestration agent in the wash water solution is the concentration level which chelates all of the hardness values and results in a small amount of excess sequestering agent.

In many applications, for example, in the home washer environment, it is impossible to select a fixed amount of sequestering agent to be added to the wash water solution in order to obtain the desired ideal sequestration. This inability to fix the needed amount of sequestering agent, even when the volume of the wash water solution is fixed, is due to variations in the concentration levels of hardness elements in the wash water solution and in the soils being removed by the wash water solution. Specifically, the amount of Ca and Mg present in surface water supplies varies seasonably in response to rainfall variations, snow melt, etc. The variation of these constituents in underground water supplies also varies for many reasons. Further, the amount of Ca and Mg present in the wash water solution is variable and increases if the soil load being removed by the wash water solution contains these elements. Many normally occurring soils do contain these hardness elements, which results in an increase in the actual concentration of both Ca and Mg from their base-line levels in the wash water supply. These added amounts of Ca and Mg also vary unpredictably with the nature and amount of soils present.

In an attempt to predict the amount of sodium tripolyphosphate sequestering agent needed to soften completely the wash water solution in a wash water apparatus, for example, a home dishwasher unit, appliance manufacturers have generally resorted to suggesting that the user start at some modest level of sequestering agent usage and then adjust the level according to the average need as perceived by the user. This trial-and-error approach obviously is unlikely to assure the use of the optimally efficient amount of sodium tripolyphosphate softener for any given wash load.

A further problem with conventional methods for softening water using sodium tripolyphosphate is that the sodium tripolyphosphate often is a component of the detergent composition being added to the wash water solution. In the case of home dishwashers, for example, sodium tripolyphosphate composes between 28-50% of the chemical ingredients in most commercially available dishwasher detergent compositions. Often, the amount that is required to be added to the wash water solution in order to achieve the desired softening level far exceeds the detergent requirements. In other words, the detergent requirements for surface activity, alkaline builders, corrosion inhibitors, suds suppressors, and chlorine carriers are not increased linearly with increased water hardness elements requiring the sodium tripolyphosphate component of the detergent composition. Thus, detergent is wasted, which is detrimental both from an economic and ecological viewpoint.

Lastly, it also would be highly beneficial both from an economic and an ecological viewpoint to be able accurately to predict on an in situ basis the amount of sodium tripolyphosphate necessary to achieve the desired softening of the wash water solution.

OBJECTS OF THE INVENTION

It is an object of the present invention to provide a method and apparatus that overcome the foregoing deficiencies and disadvantages.

It is another object of the present invention to provide a method and apparatus for achieving in situ softening of hardness elements in a wash water solution automatically irrespective of the concentration of the hardness elements.

It is a further object of the present invention to provide a method and apparatus where the sequestering agent such as sodium tripolyphosphate is supplied to the wash water solution independently of the detergent compositions.

SUMMARY OF THE INVENTION

The foregoing and other objects are attained by the method and apparatus of the present invention, which produce automatic end-point detection in a sodium tripolyphosphate water softening sequestration of a wash water solution. In one aspect of the method of the present invention, a desired approximate 1:1 molar ratio of total Ca and Mg hardness elements, calculated as $CaCO_3$, to sodium tripolyphosphate in a wash water solution is automatically detected by measuring the conductivity of the wash water solution and determining the occurrence of the maximum rate of change of conductivity of the wash water solution as the sodium tripolyphosphate is added thereto. In another aspect, the desired approximate 1:1 molar ratio is achieved by measuring the initial conductivity of the wash water solution and then by determining the occurrence of the first substantial rise in conductivity of the wash water solution, which occurs at approximately 5:2 molar ratio of calcium hardness to tripolyphosphate and then by adding 1.5 times more sodium tripolyphosphate than had been added when the substantial rise in conductivity occurred. When this maximum rate of change of conductivity occurs, the desired 1:1 molar ratio endpoint in the sodium tripolyphosphate sequestration of calcium has been achieved by the method and apparatus of the present invention, and the addition of sodium tripolyphosphate is terminated. In this latter aspect, magnesium hardness is eliminated by a pH of at least 11, which precipitates the magnesium. The pH of the wash water solution is raised to at least 11 either prior to measuring the initial conductivity or subsequent to the detection of the first substantial rise in conductivity. Apparatus is disclosed for implementing the method of the present invention by sensing the conductivity level of the wash water solution, where this sensing typically can be done at equal preselected time intervals. These measured values of conductivity are then compared, if the 5:2 molar ratio of calcium hardness to tripolyphosphate is being detected, or used to calculate delta conductivity values, which are then compared to determine whether the maximum rate of change of conductivity has occurred. In the former case, the apparatus calculates the amount of sodium tripolyphosphate which has been added, e.g., from the time period during which the adding occurred, and provides a dispensing control signal which causes 1.5 times more than that amount of sodium tripolyphosphate to be added. Base is added to raise the pH to at least 11, thereby precipitating the magnesium hardness, preferably after the 5:2 molar ratio has been detected, but it also can be raised prior to the measurement of the initial conductivity. In the latter case, when the maximum rate of change of conductivity is detected, the desired 1:1 molar ratio of hardness elements to sodium tripolyphosphate in the wash water solution has been achieved and the apparatus no longer provides a dispensing control signal to a sodium tripolyphosphate dispenser, thereby terminating the addition of the sodium tripolyphosphate to the wash water solution.

DETAILED DESCRIPTION OF THE INVENTION

We have discovered that the desired approximate 1:1 molar ratio of Ca and Mg total hardness elements to sodium tripolyphosphate ($Na_5P_3O_{10}$) sequestering agent in a wash water solution exists substantially at the point of the maximum rate of change of conductivity of the wash water solution as the sodium tripolyphosphate is added thereto and that this maximum rate of change of conductivity of the wash solution can be detected by the method and apparatus of the present invention, to provide an automatic end-point detection in the sodium tripolyphosphate sequestration, irrespective of variations of concentration levels of hardness elements in the wash water solution supply or in the soils being removed by the wash water solution.

We have also discovered that the 5:2 molar ratio of calcium hardness to sequestering agent can be detected by the first substantial rise in conductivity (above the initial conductivity) which occurs at this point, which thus permits a predetermination of the additional amount of sodium tripolyphosphate which must be added to the wash water solution to arrive at the desired 1:1 molar ratio of calcium hardness to sequestering agent. In this aspect of the present invention, the magnesium hardness is eliminated by the addition of base to the solution, preferably after the aforesaid 5:2 molar ratio is detected, thereby precipitating the magnesium ions.

The substantial rise in conductivity as used herein is defined as an increase in the range of at least about 80 $\mu$mhos above the base or starting conductivity of the wash water solution prior to the addition of the sodium tripolyphosphate thereto.

At the outset, it should be understood that the method and apparatus of the present invention relate to automated dispensing of a sodium tripolyphosphate sequestrant for complexing with water hardness constituent elements, such as Ca and Mg. The method and apparatus of the present invention have wide application because all aqueous detergent processes proceed more effectively when the hardness constituents have been removed. For example, the method and apparatus of the present invention have application in dishwashing (home and institutional), clothes washing (home and commercial), and other detergent processes carried out in aqueous media, such as car washing. For purposes of explanation only, the method and apparatus of the present invention are presented in the context of the home dishwasher environment.

Figure 1:
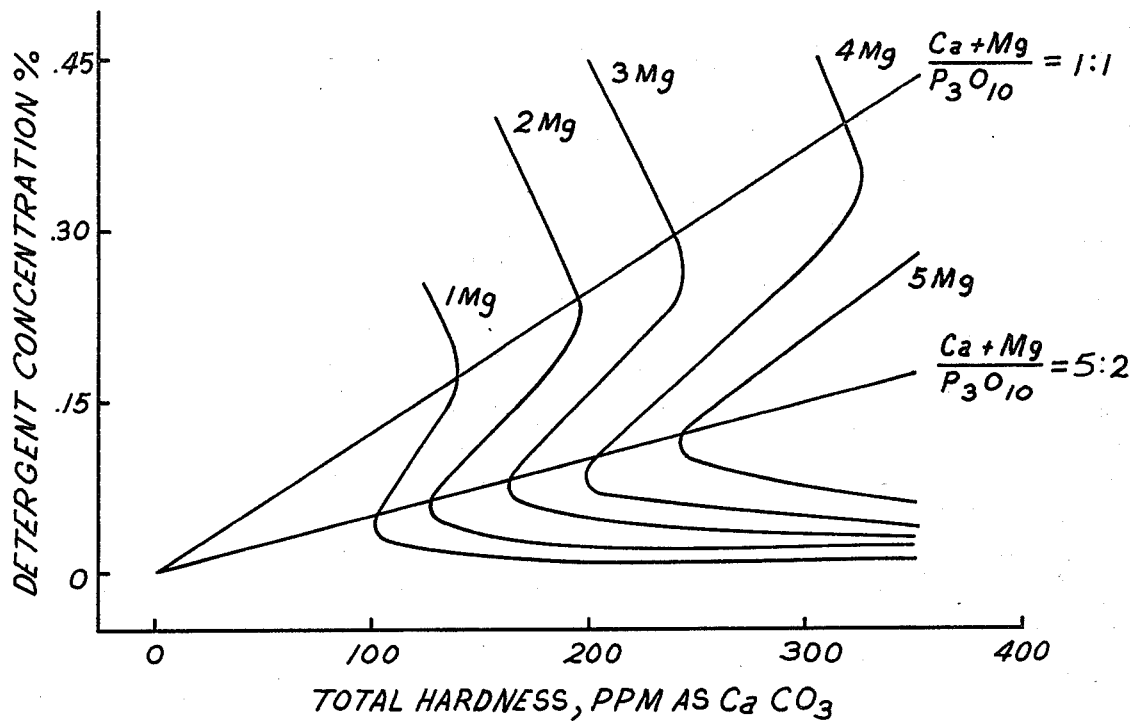
FIG. 1 is a graph plotting values of a detergent containing sodium tripolyphosphate in weight percent (wt;%) on the vertical axis for fixed values of film level in milligrams (mg) and for fixed molar ratios of hardness values to sodium tripolyphosphate with respect to values of total hardness values ($CaCO_3$) in parts per million (ppm)

An example of the importance of attaining the 1:1 molar ratio of hardness values to sodium tripolyphosphate in the wash water solution is shown by FIG. 1. FIG. 1 is a graph plotting values of concentration in wt.% in the wash water solution of a detergent composition containing sodium tripolyphosphate on the vertical axis for fixed values in mg of film levels left on glass laboratory slides washed in the wash water solution and for fixed molar ratios of hardness elements to sodium tripolyphosphate with respect to elements of total hardness values ($CaCO_3$) in ppm.

It is seen from FIG. 1 that when the wash water solution has a total hardness of 300 mg/l, a concentration of about 0.15 wt.% of detergent composition results in a heavy film of approximately 5 or more mg and the concentration must be increased to approximately 0.4 wt.% to attain the desired 1:1 molar ratio in the wash water supply and to lower substantially the film weight. This high concentration of detergent needed to achieve the desired softening, however, results in a substantial waste of detergent because the detergent requirements for surface activity, alkaline builders, corrosion inhibitors, suds suppressors, and chlorine carriers are not increased by the same amount as the required increase in detergent needed to produce the desired 1:1 molar ratio.

One proposed approach to overcome this over-use of detergent has been to separate the sodium tripolyphosphate from the detergent so that each of these two components can be added to the wash water solution independently. This approach can be utilized by the method and apparatus of the present invention.

The principle underlying one aspect of the present invention, viz., that the desired 1:1 molar ratio of total hardness elements to sodium tripolyphosphate occurs at the point of the maximum rate of change of conductivity of the wash water solution as the sodium tripolyphosphate is added thereto, can be seen from Tables 1–4, which are tables listing values of the rate of change of conductivity of the wash water solution in terms of voltage drops for specific wash water supply sources with respect to incremental amounts of sodium tripolyphosphate in mmoles added to an 8-liter wash water volume at 130° F. and with the sodium tripolyphosphate titrant having a concentration of 0.25 moles per liter $Na_5P_3O_{10}$.

The apparatus shown in FIG. 2, discussed below, detects the conductivity value of the wash water solution using an alternating current (A.C.) sensing signal. The conductivity value is indicated by the voltage drop developed across resistor 208. Because the resistor 208 is in electrical series with the electrodes 204 and 212 disposed in the wash water solution, an increase in the voltage drop across resistor 208 corresponds substantially linearly to an increase in conductivity of the wash water solution.

The conductivity exhibited during the sodium tripolyphosphate sequestration of a wash water solution having no hardness elements, i.e., a softened supply, is shown by Table 1 below. Table 1 lists the rate of change of conductivity in terms of the change in voltage drop for each incremental addition of sodium tripolyphosphate added to the wash water solution. It is seen that Table 1 supports our discovery that the desired 1:1 molar ratio occurs substantially at the point of the maximum rate of change of conductivity of the wash water solution, which in this example is at the addition of the first incremental amount of sodium tripolyphosphate.

TABLE 1

| Millimoles Ca + Mg Present | Millimoles $Na_5P_3O_{10}$ Added | Voltage Drop Across Resistor 208 in Volts | Change In Drop In Last Addition |
| --- | --- | --- | --- |
| 0 | 0.0 | 2.78 | 0.00 |
| 0 | 2.5 | 3.00 | 0.22 |
| 0 | 5.0 | 3.18 | 0.18 |
| 0 | 7.5 | 3.32 | 0.14 |
| 0 | 10.0 | 3.44 | 0.12 |
| 0 | 12.5 | 3.54 | 0.10 |

The conductivity exhibited during the sodium tripolyphosphate sequestration of a wash water solution having 9.3 millimoles of hardness elements is shown in Table 2 below. Table 2 lists the rate of change of conductivity in terms of the change in voltage drop for each addition of sodium tripolyphosphate added to the wash water solution. It can be seen from Table 2 that the desired 1:1 molar ratio occurs substantially at the point of the maximum rate of change of the conductivity of the wash water solution, which in this example is at the incremental addition of 2.5 millimoles where 7.5 millimoles has already been added to the solution.

TABLE 2

| Millimoles Ca + Mg Present | Millimoles $Na_5P_3O_{10}$ Added | Voltage Drop Across Resistor 208 in Volts | Change In Drop In Last Addition |
| --- | --- | --- | --- |
| 9.3 | 0.0 | 2.998 | 0.000 |
|  | 2.5 | 3.050 | 0.052 |
|  | 5.0 | 3.124 | 0.074 |
|  | 7.5 | 3.239 | 0.115 |
|  | 10.0 | 3.372 | 0.133 |
|  | 12.5 | 3.500 | 0.128 |
|  | 15.0 | 3.621 | 0.121 |

The conductivity exhibited during the sodium tripolyphosphate sequestration of a wash water solution having an estimated 12.4 millimoles of hardness elements is shown in Table 3 below. The solution of Table 3 comprises 9.3 millimoles of hardness elements plus 8 grams of powdered milk, which together constitutes an estimated 12.4 millimoles of hardness elements based on the U.S.D.A. Agricultural Handbook No. 8 (1975). Table 3 lists the rate of change of conductivity in terms of the change in voltage drop for each addition of sodium tripolyphosphate added to the wash water solution. It can be seen from Table 3 that the desired 1:1 molar ratio occurs substantially at the point of the maximum rate of change of the conductivity of the wash water solution, which in this example is at the incremental addition of 2.5 millimoles where 10.0 millimoles has already been added to the solution.

TABLE 3

| Millimoles Ca + Mg Present | Millimoles $Na_5P_3O_{10}$ Added | Voltage Drop Across Resistor 208 in Volts | Change In Drop In Last Addition |
| --- | --- | --- | --- |
| 12.4 | 0.0 | 3.065 | 0.000 |
|  | 2.5 | 3.113 | 0.048 |
|  | 5.0 | 3.185 | 0.072 |
|  | 7.5 | 3.301 | 0.116 |
|  | 10.0 | 3.417 | 0.116 |
|  | 12.5 | 3.537 | 0.120 |
|  | 15.0 | 3.641 | 0.104 |
|  | 17.5 | 3.736 | 0.095 |

The conductivity exhibited during the sodium tripolyphosphate sequestration of a wash water solution having an estimated 15.3 millimoles of hardness elements is shown in Table 4. Table 4 lists the rate of change of conductivity in terms of the change in voltage drop for each addition of sodium tripolyphosphate added to the wash water solution. It can be seen from Table 4 that the desired 1:1 molar ratio occurs substantially at the point of the maximum rate of change of conductivity of the wash water solution, which in this example is at the incremental addition of 2.5 millimoles where 15.0 millimoles has already been added to the solution.

TABLE 4

| Millimoles Ca + Mg Present | Millimoles $Na_5P_3O_{10}$ Added | Voltage Drop Across Resistor 208 in Volts | Change In Drop In Last Addition |
| --- | --- | --- | --- |
| 15.3 | 0.0 | 2.940 | 0.000 |
|  | 2.5 | 2.968 | 0.028 |
|  | 5.0 | 2.991 | 0.023 |
|  | 7.5 | 3.033 | 0.042 |

TABLE 4-continued

| Millimoles Ca + Mg Present | Millimoles Na$_5$P$_3$O$_{10}$ Added | Voltage Drop Across Resistor 208 in Volts | Change In Drop In Last Addition |
|---|---|---|---|
| | 10.0 | 3.111 | 0.078 |
| | 12.5 | 3.218 | 0.107 |
| | 15.0 | 3.329 | 0.111 |
| | 17.5 | 3.433 | 0.104 |
| | 20.0 | 3.533 | 0.100 |

In this aspect of the present invention, the maximum rate of change of conductivity of the wash water solution, which substantially occurs at a 1:1 molar ratio of hardness elements to sodium tripolyphosphate, is detected by calculating and comparing the delta voltage drop values (which correspond to the delta conductivity values), and detecting when a preselected plurality of succeeding delta voltage drop levels are less than the next preceding delta voltage drop level.

As stated above, in another aspect of the present invention, the 5:2 molar ratio of a calcium hardness to sequestering agent can be detected by the substantial rise in conductivity in the wash water which occurs at this ratio. A substantial rise in conductivity as used herein means an increase in the range of at least about 80 μmhos above the initial or starting conductivity of the wash water solution prior to the addition of the sodium tripolyphosphate to the solution. A convenient detection range is about 100-150 μmhos, preferably about 100-125 μmhos. In the case where the pH of the wash water solution is raised to at least 11 prior to the addition of the sodium tripolyphosphate thereto, the initial conductivity is determined after the pH is raised. The desired 1:1 molar ratio thereafter is achieved by adding 1.5 times sodium tripolyphosphate than had been added to reach the detected 5:2 molar ratio, or, in the case where the ON time is measured, continuing the addition until the total ON dispensing time is equal to 2.5 times the ON time required to reach the 5:2 molar ratio. Because the 5:2 molar ratio of magnesium hardness to sequestering agent cannot be detected, the magnesium hardness is eliminated in this aspect of the invention by raising the pH of the wash water to above 11, thereby precipitating the magnesium ions, preferably after detecting the 5:2 ratio of calcium hardness to sequestering agent, so as to provide a lower baseline conductivity.

We have found in this aspect of the present invention that calcium and not magnesium is the primary factor responsible for the change in conductivity of the wash water solution due to the addition of sodium tripolyphosphate to reach the 5:2 molar ratio. Further, it is well known the magnesium is insoluble in alkaline solutions and thus precipitates as the hydroxide. Because the ion product constant of this hydroxide compound is very small ($K_{sp} = 1.2 \times 10^{-11}$), the concentration of magnesium ion becomes vanishingly small at pH values above 11, thereby eliminating the magnesium ions as a source of hardness.

Consequently, in order to avoid the use of excess sequestering agent, to ensure the elimination of all hardness elements in the wash water because of an inability to determine the amount of magnesium ions present therein at the 5:2 molar ratio level of sequestering agent, the pH of the wash water solution is raised to at least about 11, preferably at or after the point where the 5:2 molar ratio of calcium hardness to tripolyphosphate is detected by the substantial rise in the conductivity. However, the pH can be raised to at least 11 prior to the measurement of the initial conductivity. The sodium tripolyphosphate thus sequesters only the calcium in the wash water solution at the desired 1:1 molar ratio.

The principle underlying this aspect of the present invention, viz., that the 5:2 molar ratio of calcium hardness to sodium tripolyphosphate occurs at the point of the substantial rise in conductivity of the wash water solution as the sodium tripolyphosphate is added thereto, can be seen from Tables 5-7 below, which list values of conductivity of the wash water solution in μmhos for specific wash water supply sources with respect to values of sodium tripolyphosphate in mmoles for an 8-liter wash water volume at 130° F., with a sodium tripolyphosphate titrant having a concentration of 0.25 mole per liter Na$_5$P$_3$O$_{10}$.

The conductivity exhibited during the sodium tripolyphosphate sequestration of a wash water solution having 10.0 millimoles of hardness elements is listed in Table 5 below, which lists the change in conductivity from the base conductivity value, for each addition of sodium tripolyphosphate added to the wash water solution. It is seen from Table 5 that the 5:2 molar ratio of calcium ions to sequestering agent occurs at the point of the first substantial rise in conductivity (above about 80 μmhos) above the base conductivity value.

TABLE 5

| Millimoles Ca Present | Millimoles Na$_5$P$_3$O$_{10}$ Added | Conductivity Value In μmhos | Change In Conductivity From Base Value In μmhos |
|---|---|---|---|
| 10 | 0 | 300 | — |
| | 2 | 345 | +45 |
| | 4 | 385 | +85 |
| | 6 | 475 | +175 |
| | 8 | 580 | +280 |
| | 10 | 715 | +415 |
| | 12 | 840 | +540 |
| | 14 | 950 | +650 |
| | 16 | 1020 | +720 |

The conductivity exhibited during the sodium tripolyphosphate sequestration of a wash water solution having 20.0 millimoles of hardness elements is listed in Table 6 below. Table 6 lists the change in conductivity from the base conductivity value for each addition of sodium tripolyphosphate added to the wash water solution. It can be seen from Table 6 that the 5:2 molar ratio occurs at the point of the first substantial rise in conductivity, which in this example is a rise of about 100 μmhos above the base conductivity value.

TABLE 6

| Millimoles Ca Present | Millimoles Na$_5$P$_3$O$_{10}$ Added | Conductivity Value In μmhos | Change In Conductivity From Base Value In μmhos |
|---|---|---|---|
| 20 | 0 | 560 | — |
| | 2 | 580 | +20 |
| | 4 | 600 | +40 |
| | 6 | 625 | +65 |
| | 8 | 660 | +100 |
| | 10 | 725 | +165 |
| | 12 | 800 | +240 |
| | 14 | 880 | +340 |
| | 16 | 975 | +415 |
| | 18 | 1075 | +515 |
| | 20 | 1160 | +600 |
| | 22 | 1250 | +690 |
| | 24 | 1325 | +765 |

The conductivity exhibited during the sodium tripolyphosphate sequestration of a wash water solution having 30.0 millimoles of hardness elements is listed in Table 7 below. Table 7 lists the changes in conductivity from the base conductivity value for each addition of sodium tripolyphosphate added to the wash water solution. It can be seen from Table 7 that the 5:2 molar ratio occurs at the point of the first substantial rise in conductivity, which in this example is a rise of about 90 μmhos above the base conductivity value.

TABLE 7

| Millimoles Ca Present | Millimoles $Na_5P_3O_{10}$ Added | Conductivity Value In μmhos | Change In Conductivity From Base Value In μmhos |
|---|---|---|---|
| 30 | 0 | 940 | — |
| | 2 | 955 | +15 |
| | 4 | 960 | +20 |
| | 6 | 970 | +30 |
| | 8 | 975 | +35 |
| | 10 | 985 | +45 |
| | 12 | 1030 | +90 |
| | 14 | 1090 | +150 |
| | 16 | 1175 | +235 |
| | 18 | 1260 | +320 |
| | 20 | 1340 | +400 |
| | 22 | 1430 | +490 |
| | 24 | 1500 | +560 |
| | 26 | 1580 | +640 |

In carrying out the method of the present invention, the sodium tripolyphosphate can be dispensed to the dish, laundry or other type of washer as a component of a detergent composition, or can be dispensed separately from any detergent dispensed thereto during the wash cycle. In the former case, unless a sodium tripolyphosphate-free detergent composition is also added separately to the wash water solution, the concentration of the sodium tripolyphosphate in the detergent composition should be such as to ensure that an adequate, but not an excessive, amount of detergent is concurrently added with the sodium tripolyphosphate. For areas having relatively soft water, a concentration of sodium tripolyphosphate of about 29–35 wt.% in the detergent composition is preferred; in areas having relatively hard water, a concentration of about 40–50 wt.% therein is preferred. However, because the presence of detergent in the sequestration process of this invention is optional, the exact concentration of the sodium tripolyphosphate in a detergent composition employed in the process of this invention is not critical. As would be apparent, if the detergent composition contains builders or other sources of ions, their effect on conductivity will have to be taken into consideration, particularly in the aspect of this invention in which the 5:2 molar ratio of calcium hardness to tripolyphosphate is detected. Preferably, these other sources of ions should not be supplied to the wash water until the first substantial rise in conductivity has been detected.

The sodium tripolyphosphate can be dispensed in solid form or in the form of a liquid solution. For a description of conventional liquid and solid dispensers, see "Industrial Detergency", edited by Niven of MRI (1955), pages 229–233.

The sodium tripolyphosphate can be dispensed to the wash water solution either intermittently or continuously, but at a rate slow enough to permit the determination of the effect upon the conductivity of the wash water solution of sequential incremental amounts of the sodium tripolyphosphate and to permit termination of dispensing, when a specific effect is detected, before an amount of sodium tripolyphosphate substantially in excess of the desired optimum is dispensed. In a dishwasher application, the sodium tripolyphosphate is dispensed at a rate per second of preferably about 4–12; more preferably 7–9 mg/l of the wash water solution.

If the sodium tripolyphosphate is dispensed continuously it is important that the dispensing device is positioned downstream of the conductivity measuring device to ensure that the dispensing sodium tripolyphosphate is uniformly distributed throughout the wash water solution before the conductivity is measured. When the sodium tripolyphosphate is dispensed intermittently, the dispensing and conductivity measuring devices can be positioned proximate to each other if conductivity is measured after each increment of dispensed sodium tripolyphosphate has become uniformly distributed throughout the wash water solution.

When the sodium tripolyphosphate is dispensed continuously, it preferably is dispensed at a uniform rate and the conductivity of the wash water solution is measured at predetermined uniform time intervals, thereby providing a constant base against which changes in conductivity can be related. However, it is also possible to employ a system in which the sodium tripolyphosphate is added continuously but at rates which vary in a predetermined manner during the addition period and the time spans between successive conductivity measurement varies inversely proportionately thereto, thereby maintaining constant the incremental amount of sodium tripolyphosphate which is added between each conductivity measurement. For example, during the initial portion of the addition period, the sodium tripolyphosphate can be added at a rate which is 2–10 times as great as that of the final portion of the addition period and the frequency of the conductivity measurements can be increased proportionately, viz., 2–10 times as often, during the initial portion of the addition period. Similarly, when the sodium tripolyphosphate is added intermittently, in increments rather than continuously, the size of the increments during the initial portion of the addition period can be 2–10 times as large as those during the final portion of the addition period, and the value assigned to the change in conductivity during the final period is increased proportionally, viz., 2–10 times the actual change in conductivity which occurs after each incremental addition of sodium tripolyphosphate during the final period.

The process and apparatus of this invention can also be used to determine when to terminate the rinsing cycles, e.g., by comparing the conductance of the waste rinse water with fresh rinse water and terminating rinsing when the values are approximately the same, thus establishing the absence of substantial amounts of sodium tripolyphosphate in the waste rinse water.

As stated above, the method of the present invention determines the amount of required sodium tripolyphosphate for sequestration so as to achieve a 1:1 molar ratio between the hardness elements and the sodium tripolyphosphate, either in one aspect by sensing the maximum rate of change of conductivity of the wash water solution as the sodium tripolyphosphate is added, or, in another aspect by sensing the first substantial rise in conductivity from the initial conductivity which occurs at the 5:2 molar ratio of calcium hardness to tripolyphosphate, and then adding 1.5 times more sodium tripolyphosphate than had been added to reach the 5:2 molar ratio or, in the case where the ON time is measured for the addition of sodium tripolyphosphate to reach the 5:2 molar ratio, dispensing sodium tripolyphosphate at the same rate to the solution so that the total ON dispensing time is equal to 2.5 times the ON time required to reach the 5:2 molar ratio, and adding sufficient base to reach a pH of at least 11. The process of the present invention can thus achieve the desired 1:1 molar ratio between the hardness values and the sodium tripolyphosphate, irrespective of variations of concentration levels of hardness values in the wash water supply or in the soils being removed by the wash water solution.

Figure 2:
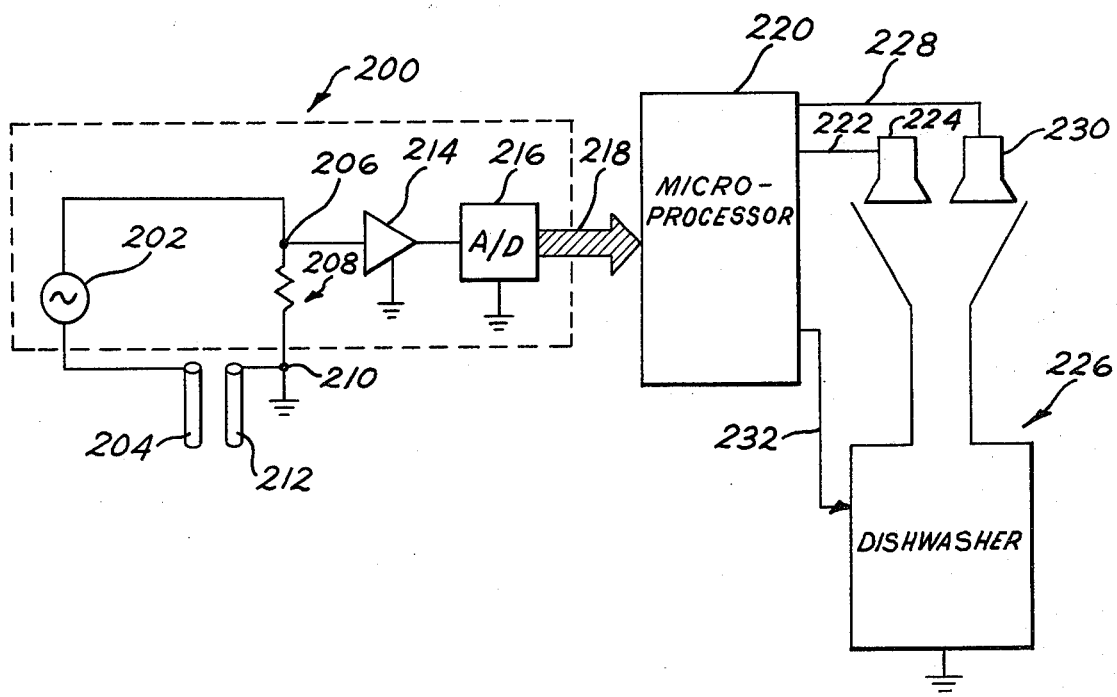
FIG. 2 is a block diagram of apparatus according to the present invention.

An embodiment of the apparatus for implementing the method of the present invention is shown in block diagram form in FIG. 2. In should be understood that this embodiment is only illustrative, and that any apparatus can be employed to implement the method of the present invention if the apparatus is capable of accurately sensing the conductivity of the wash water solution being sequestrated and is capable of controlling the dispensing of the sequestration component to the wash water solution in accordance with the sensed conductivity and a stored program control.

As shown in FIG. 2, a conductivity measurement circuit is contained within the dashed-lined box designated generally by reference numeral 200. Circuit 200 includes a voltage source 202 of alternating voltage connected to a conductivity electrode 204 and to one side 206 of a resistor designated generally by reference numeral 208. The other side 210 of resistor 208 is connected both to electrical ground and to a conductivity electrode 212. The voltage drop produced by resistor 208 in electrical series connection with conductivity electrodes 204 and 212 is directly proportional to the conductivity of the solution (not shown) being sensed by conductivity electrodes 204 and 212.

The voltage signal at side 206 of resistor 208 is supplied to an amplifier 214 of conventional design, which amplifies the voltage signal and supplies it to the input of an analog to digital converter 216. Analog to digital converter 216 is of conventional design and converts the voltage signal to a digital representation which is supplied to a signal buss 218. This signal on buss 218, which is designated the conductivity signal, can have any desired digital format, such as binary or binary coded decimal (BCD).

The conductivity signal on buss 218 is supplied as an input signal to a microprocessor 220. Microprocessor 220 provides a dispensing signal on a line 222 to a dispenser 224 of conventional design, which dispenses sodium tripolyphosphate on receipt of the dispensing signal to a dishwasher designated generally by reference numeral 226. In addition, microprocessor 220 provides a level signal on a line 228 to a dispenser 230 of conventional design, which on receipt of the level signal dispenses a base chemical to the dishwasher 226. Further, microprocessor 220 provides a control signal on a line 232 to dishwasher 226 for control of the operation of dishwasher 226. Dishwasher 226 can be of any type adapted to accommodate the dispensers 224 and 230 and the conductivity electrodes 204 and 212. One dishwasher suitable for modification is the Model GSD 950 dishwasher made by the General Electric Company.

Microprocessor 220 can be of any suitable type that under stored program implements the method of the present invention in either the 1:1 aspect or the 5:2 aspect, as is discussed in detail below. For example, microprocessor 220 can be an F8 made by Mostek of Carrollton, Tex. Alternately, microprocessor 220 could be custom integrated circuit or gate array circuit fabricated or modified so that it implements the method of the present invention.

Figure 3:
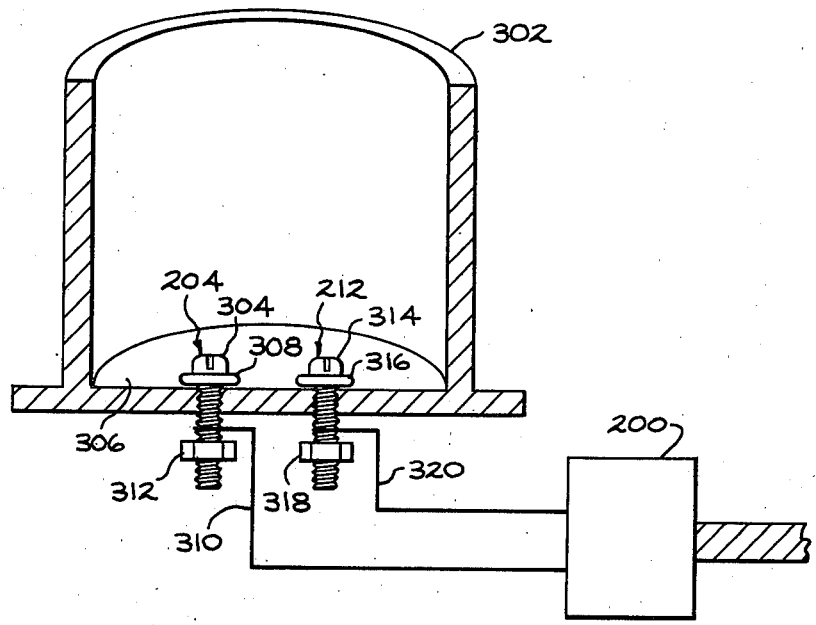
FIG. 3 is a partial perspective view of an embodiment of the conductivity sensor electrodes.

Referring now to FIG. 3, a suitable arrangement for providing conductivity electrodes 204 and 212 within dishwasher 226 is shown. Conductivity electrodes 204 and 212 are identical, and they are disposed a preselected distance (for example, one inch) from each other in a dishwasher sump plug 302. It should be noted that any suitable spacing distance for electrodes 204 and 212 can be used, such as, for example, one inch. Electrode 204 comprises a bolt 304, preferably of stainless steel, mounted in a nonconductive base 306 of plug 302. A gasket 308, of a suitable material such as rubber, is disposed between the head of bolt 304 and base 306 to provide a fluid seal. A nut 312, preferably of stainless steel, is tightened down (not shown) to secure electrically a lead 310 to bolt 304 and to compress gasket 308. Electrode 212 has the same structure as electrode 204, and comprises a bolt 314, a gasket 316 and a nut 318, which when tightened down (not shown) electrically secures a lead 320 to bolt 314 and compresses gasket 316. Leads 310 and 320 are electrically connected to the conductivity measurement circuit 200 of FIG. 2.

It has been found that conductivity sensors 204 and 212 should be disposed in dishwasher 226 so that they are accessible and in full contact with the wash water solution during conductivity measurements. It was found that sudsing or splashing can cause erroneous measurements. While graphite has been used for the conductivity electrodes, a good grade of stainless steel completely submerged below the level of the splashing and sudsing has been found to give reproducible conductivity measurements.

Figure 4:
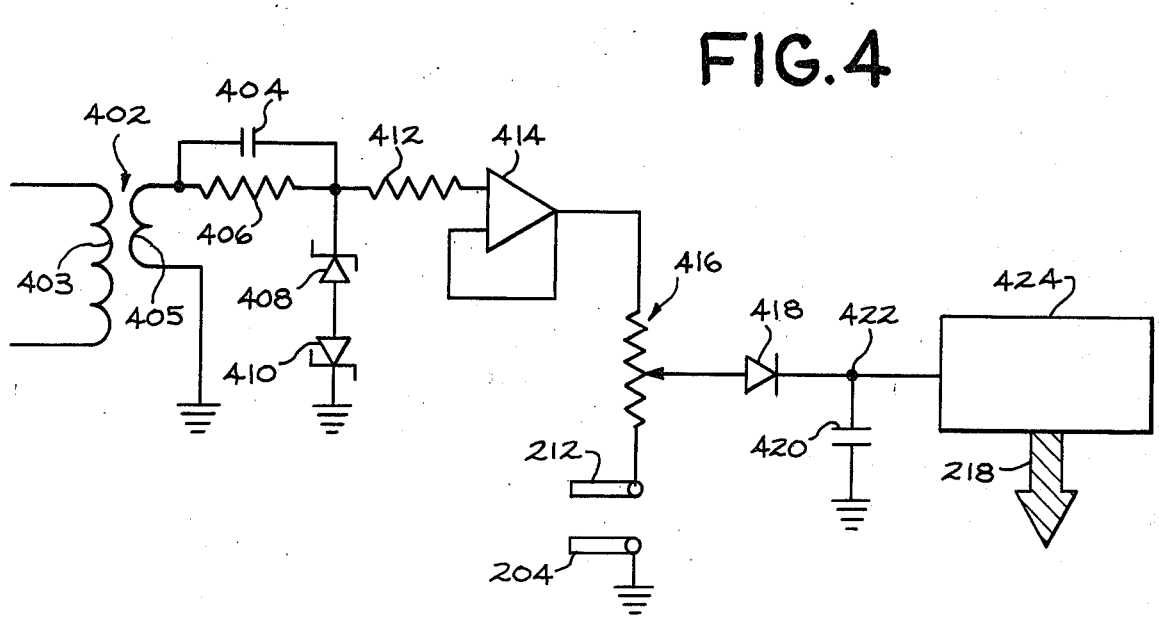
FIG. 4 is a schematic diagram of the conductivity measurement circuit 200 of FIG. 2.

A more detailed schematic representation of the conductivity measurement circuit 200 of FIG. 2 is shown in FIG. 4. Identical reference numbering indicates the same component.

The voltage source 202 of FIG. 2 comprises in FIG. 4, transformer 402, capacitor 404, resistor 406, Zener diodes 408 and 410, resistor 412 and operational amplifier 414. The primary winding 403 of transformer 402 is connected to a suitable A.C. power source (not shown), while the secondary winding 405 is connected to capacitor 404 and resistor 406. The secondary winding can provide any selected A.C. voltage, such as 12.6 volts. Capacitors 404, resistor 406 and Zener diodes 408 and 410 are connected so as to operate as a clipper circuit that provides a clipped waveform A.C. signal having a selected amplitude (such as 4.7 volts) which has a fairly constant amplitude over slight power source (not shown) voltage variations. The clipped waveform A.C. voltage is fed through resistor 412 to bipolar operational amplifier 414 connected to operate as a voltage follower. Operational amplifier 414 acts as a buffer to supply the clipped waveform voltage to potentiometer 416 (which corresponds to resistor 208) and to conductivity electrodes 204 and 212.

The center or wiper arm of potentiometer 416 provides a clipped waveform A.C. voltage signal having an amplitude value which is directly proportional to the conductivity of the wash water solution (not shown) being sensed by electrodes 212 and 204. This voltage signal is provided to a rectifier network comprising a diode 418 and a capacitor 420, which are connected to provide D.C. signal at a node 422 having an amplitude directly proportional to the A.C. signal being rectified. The D.C. signal at node 422 is provided to the input of analog-to-digital converter and display 424 of conventional design, which provides both a parallel 8 bit digital conductivity signal on buss 218 and also provides a visual signal indication (not shown) of the voltage level of the D.C. signal.

It should be noted that microprocessor 220 of FIG. 2 can be responsive to the complete digital conductivity signal provided by buss 218 (irrespective of whether this digital signal is in serial or parallel format), or can be responsive to only certain portions of the digital signal. In the disclosed embodiment, microprocessor 220 is responsive only to the four bits representative of the most significant digits of the digital signal.

Figure 5:
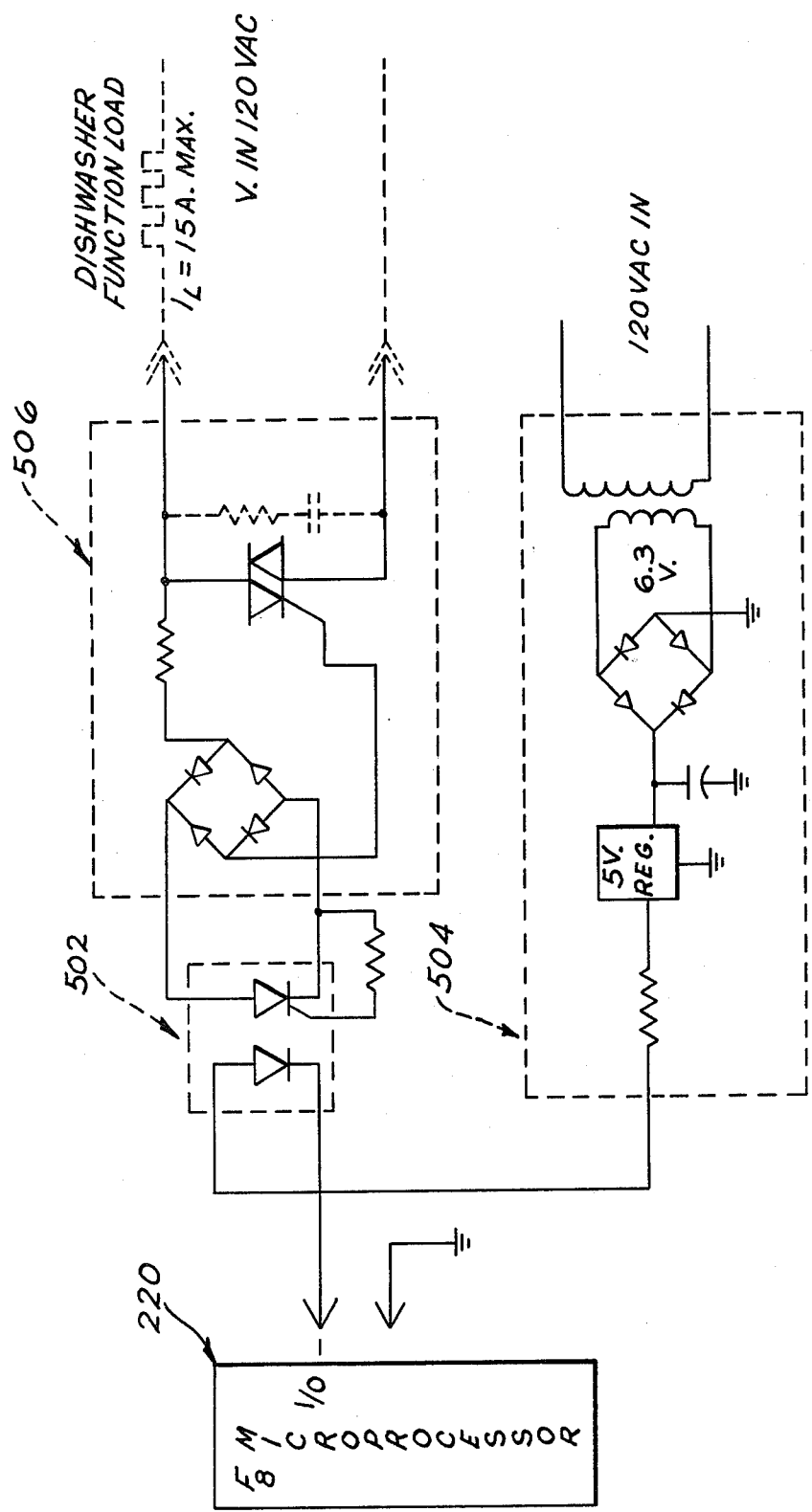
FIG. 5 is a schematic diagram of interface electronics between the microprocessor and the controlled devices of FIG. 2.

A schematic of a representative circuit for interfacing the output of the microprocessor 220 of FIG. 2 with dispenser 224, dispenser 230 or the operational functions of dishwasher 226 (not shown) with respect to the control signal on line 232 is shown in FIG. 5. An optical coupler 502 of conventional design (such as a General Electric H-11C) is connected to the output port of microprocessor 220. Coupler 502 is provided a D.C. driving voltage of selected voltage (for example 5 volts D.C.) by a D.C. voltage source, such as the conventional full wave rectifier and regulator circuit shown within dash-lined box 504. The optically controlled SCR of coupler 502 controls a TRIAC switch 506 of conventional design shown within dash-lined box. The output of TRIAC switch 506 corresponds to the output of the respective output port of microprocessor 220 but can be used to control a high voltage load.

Figure 6:
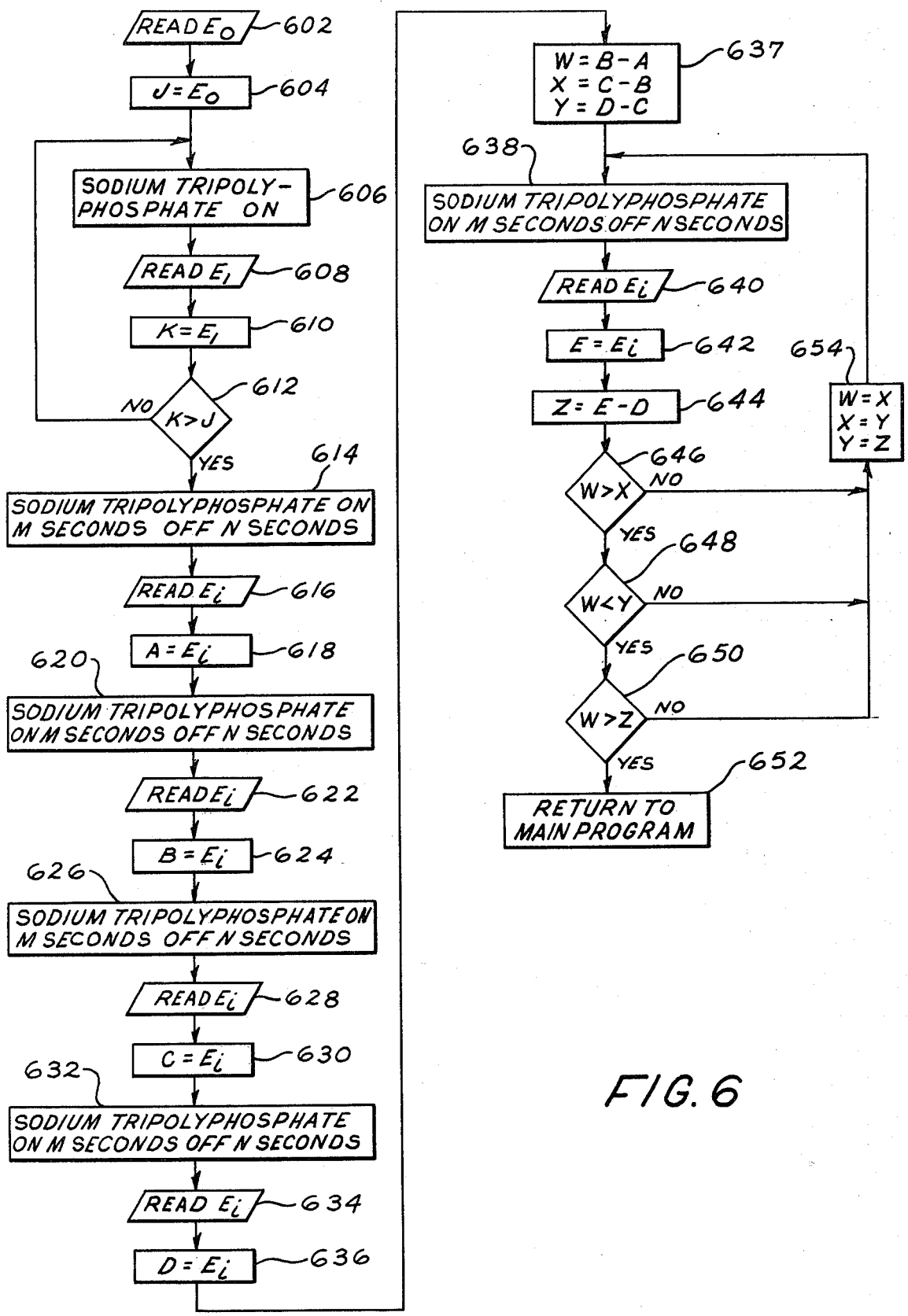
FIG. 6 is a flow chart relating to the 1:1 molar ratio aspect of the present invention.

Referring now to FIG. 6, a flow chart is shown for the operation of the microprocessor 220 in accordance with the first aspect of the present invention where the desired 1:1 molar ratio is detected by the occurrence of three succeeding data conductivity values being less than the next preceding delta conductivity value. The operation of the apparatus in accordance with the method of the present invention is as follows. The initial or base conductivity value $E_o$ of the wash water solution is measured, as indicated by block 602, and then stored for later use, as indicated by block 604. The sodium tripolyphosphate is then dispensed for a preselected period of time, such as M second, as indicated by block 606. Thereafter, the conductivity value $E_1$ of the solution is measured, as indicated by block 608, and then stored for later use, as indicated by block 610. Then, the conductivity value K is compared to the conductivity value J, as indicated by decisional block, 612, and if $K \leq J$, then a do loop returns the program to the step 606.

Thus, it is seen that sodium tripolyphosphate is added to the solution in accordance with this do loop until $K > J$. Once $K > J$, the do loop is exited and the addition of sodium tripolyphosphate to the solution is made for M seconds and then is stopped for N seconds (the N time period allows the wash water solution to return to a stable conductivity state), as indicated by block 614. After the time lapse of N seconds, the conductivity value $E_i$ of the solution is measured, as indicated by block 616, and then stored for later use, as indicated by block 618. Then, sodium tripolyphosphate is added to the solution for M seconds, and then is stopped for N seconds, as indicated by block 620. Thereafter, the conductivity value $E_i$ of the solution is measured, as indicated by block 622, and then stored for later use, as indicated by block 624. Then, sodium tripolyphosphate is added to the solution for M seconds and then is stopped for N seconds, as indicated by block 626. Thereafter, the conductivity value $E_i$ of the solution is measured, as indicated by block 628, and then stored for later use, as indicated by block 630. Then, sodium tripolyphosphate is added to the solution for M seconds and then is stopped for N seconds, as indicated by block 632. Thereafter, the conductivity value $E_i$ of the solution is measured, as indicated by block 634, and then stored for later use, as indicated by block 636.

The three delta conductivity values W, X and Y are then determined, as indicated by block 637. Specifically, the oldest (denominated the next preceding) delta conductivity value W is computed by subtracting the A conductivity value from the B conductivity value, the next oldest (first succeeding) delta conductivity value X is computed by subtracting the B conductivity value from the C conductivity value, and the second succeeding delta conductivity value Y is computed by subtracting the C conductivity value from the D conductivity value. Then, sodium tripolyphosphate is added to the solution for M seconds and then is stopped for N seconds, as indicated by block 638. Thereafter, the conductivity value $E_i$ of the solution is measured, as indicated by block 640, and then stored for later use, as indicated by block 642.

Then, the newest or third succeeding delta conductivity value Z is computed by subtracting the D conductivity value from the E conductivity value, as indicated by block 644. Then, the oldest conductivity value W is compared with the X, Y and Z delta conductivity values, as indicated respectively by decisional blocks 646, 648 and 650, and the desired 1:1 molar ratio is detected if $W > X$, $W > Y$, and $W > Z$, whereupon microprocessor 220 returns to the main program, as indicated by block 652.

In other words, three succeeding delta conductivity values which are less than the next preceding conductivity value indicates that the maximum rate of change of conductivity has been detected.

If, however, the maximum rate of change of conductivity has not been detected, as indicated by W being less than one or more of the X, Y and Z values, then the oldest delta conductivity value W is discarded, and the other delta conductivity value are substituted for the W, X and Y values, respectively, as shown by block 654. Then, a do loop returns the microprocessor 220 to step 638, which causes more sodium tripolyphosphate to be added to the solution and thereafter a new delta conductivity value Z to be computed. The do loop is repeated until the W value is greater than the X, Y, and Z values.

While four delta conductivity values W, X, Y and Z are computed and compared to detect the desired 1:1 molar ratio, it should be understood that the present invention can detect the desired 1:1 molar ratio where at least two delta conductivity values are computed and compared. Further, the time intervals N+M seconds between conductivity value can be as short or as long as desired, provided that in the minimum the solution has sufficient time to return to a relatively constant conductivity state. A representative time interval between conductivity samples is 40 seconds.

Figure 7:
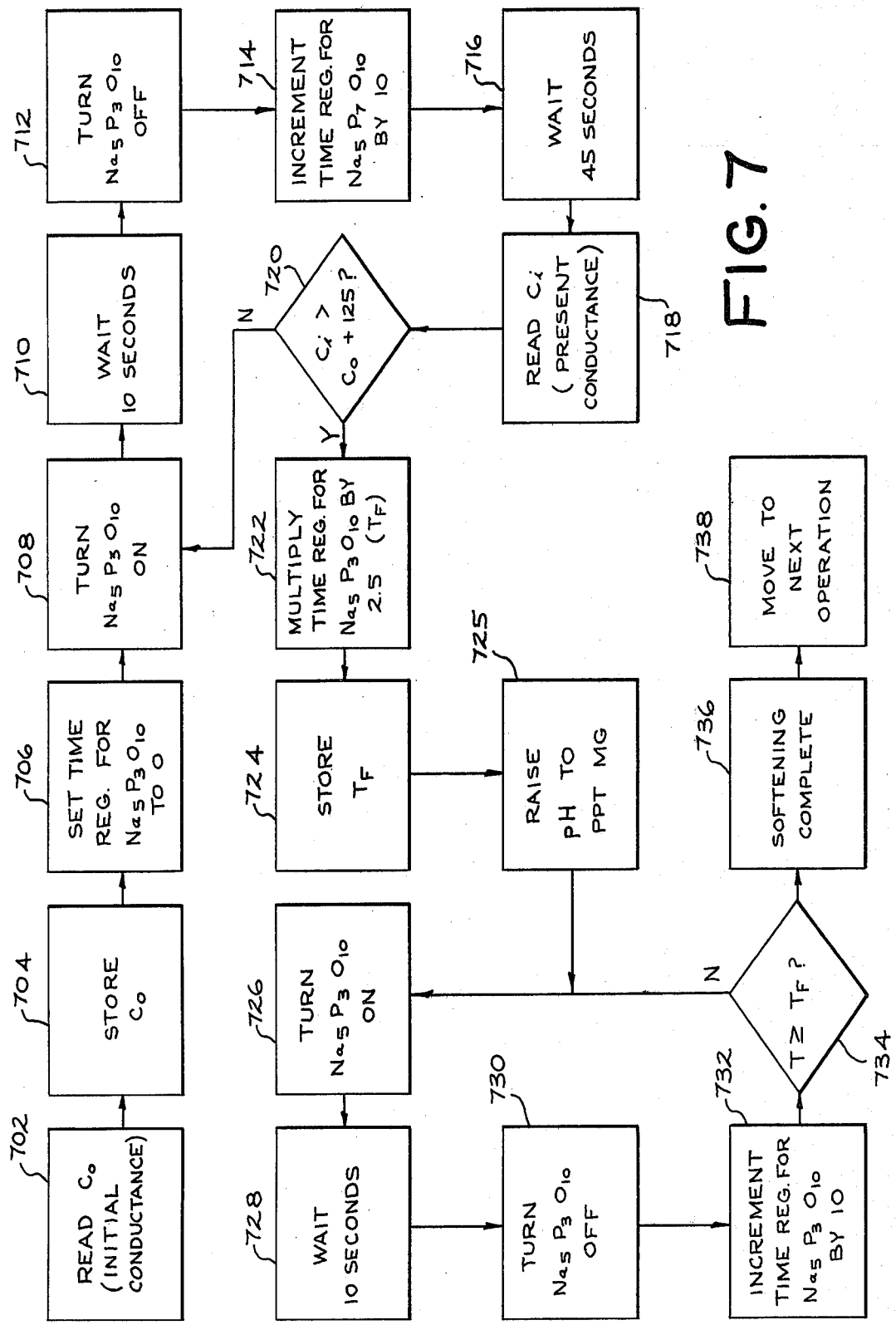
FIG. 7 is a flow chart relating to the 5:2 molar ratio aspect of the present invention.

Referring now to FIG. 7, a flow chart is shown for operation of microprocessor 220 in accordance with the second aspect of the present invention where the 5:2 molar ratio is detected by the first substantial rise in conductivity above the initial conductivity of the wash water solution. This first substantial rise is detected when the increase in the conductivity value $C_i$ of the solution due to the addition of sodium tripolyphosphate thereto above the initial conductivity value $C_o$ of the solution prior to the addition of the sodium tripolyphospate at least equal to a predetermined magnitude which preferably is at least 80 μmhos. In the embodiment of FIG. 7, a substantial rise is detected when the increase in conductivity is more than 125 μmhos.

As shown in FIG. 7, the starting or initial conductivity value $C_o$ of the wash water solution is measured, as indicated by block 702, and then stored, as indicated by block 704. The initial conductivity is measured prior to the addition of the sodium tripolyphosphate to the wash water solution, and subsequent to the addition of the base used to raise the pH of the wash water solution to at least 11 where the pH is raised prior to the addition of sodium tripolyphosphate (not shown in FIG. 7). Then a sodium tripolyphosphate time register is initialized to zero, as indicated by block 706. After the initialization, the sodium tripolyphosphate is added to the solution for a ten second period of time, as indicated by blocks 708 and 710. Thereafter, the sodium tripolyphosphate is turned OFF, as indicated by block 712, and the time register is incremented up by a 10 second value, as indicated by block 714. Then, the sodium tripolyphosphate is not added for 45 seconds to allow the solution to return to conductivity equilibrium, as indicated by block 716. Thereafter, the conductivity value $C_i$ of the solution is measured, as indicated by block 718. This conductivity value $C_i$ is then compared with the initial conductivity value $C_o$, as indicated by decisional block 720, and in the case where $C_i \leq C_o + 125$, a do loop returns the program to block 708. Thus, sodium tripolyphosphate is added to the solution until the first substantial rise in conductivity is indicated by the relationship $C_i > C_o + 125$.

When $C_i > C_o + 125$, the value stored in the time register is multiplied by 2.5 to produce a time value $T_f$, as indicated by block 722. The $T_f$ value is stored, as indicated by block 724, and then the pH of the wash water solution is raised to a value of at least 11 by the addition of a chemical base, as indicated by block 725. Once the pH has been raised, the sodium tripolyphosphate is added to the solution for 10 seconds, as indicated by blocks 726, 728 and 730, and the time register is incremented by a 10 second value, as indicated by block 732. The time value T of the time register is compared with the $T_f$ value, as indicated by decisional block 734. If $T < T_f$ a do loop returns microprocessor 220 to step 726 of the program.

When $T \geq T_f$, which indicates that 1.5 times more sodium tripolyphosphate has been added to the solution than that required to reach the 5:2 molar ratio as detected by the first substantial rise in conductivity, then the microprocessor 220 is caused to return to the main dishwashing program as indicated by blocks 736 and 738.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

Example 1

A solution containing 92 grams per liter sodium tripolyphosphate in distilled water was added to 8 liters of softened tap water contained and circulating in a General Electric GSD-950-01 dishwasher. The temperature of the circulating water was 54.4° C. Additions of sodium tripolyphosphate solution were made in 10 ml. increments, at a rate of 2 ml. per second. The voltage drop across a 464 ohm resistor was recorded 10 seconds after each incremental addition. The values obtained are given below:

| Increment | Millimoles Na$_5$P$_3$O$_{10}$ Present | Voltage Drop | Delta Voltage Drop |
|---|---|---|---|
| 0 | 0.00 | 2.787 | .000 |
| 1 | 2.50 | 2.989 | .202 |
| 2 | 5.00 | 3.172 | .183 |
| 3 | 7.50 | 3.313 | .141 |

Since softened water was used, no hardness was present and the control logic correctly interpreted the first addition as the end-point and the addition of sodium tripolyphosphate was terminated after the third increment because the delta voltage drop obtained after the second increment correctly established that the delta voltage drop after the first increment was the largest. The control logic could have, if desired, terminated the additions after the second increment. However, to ensure that incremental additions are not prematurely terminated because of a spurious high value, the control logic was programmed to confirm that a maximum delta voltage drop had been achieved by requiring two successive lower values after the higher value.

Example 2

A solution containing 92 grams per liter of sodium tripolyphosphate in distilled water was added to 8 liters of tap water (54.2° C.) circulating in a General Electric GSD-950-01 dishwasher. Incremental additions of 5 ml. were made, with the voltage drop across a 464 delta resistor being recorded after the fifth increment 10 seconds after each incremental addition. Total millimoles hardness present was 9.3.

| Increment | Millimoles Na$_5$P$_3$O$_{10}$ Present | Voltage Drop | Delta Voltage Drop |
|---|---|---|---|
| 0 | 0.00 | 2.998 | .000 |
| — | — | — | — |
| — | — | — | — |
| — | — | — | — |
| — | — | — | — |
| 5 | 6.25 | 3.176 | — |
| 6 | 7.50 | 3.239 | .063 |
| 7 | 8.75 | 3.304 | .065 |
| 8 | 10.00 | 3.372 | .068 |
| 9 | 11.25 | 3.436 | .064 |
| 10 | 12.50 | 3.500 | .064 |

Control logic correctly interpreted the eighth incremental addition as the end-point and addition of the sodium tripolyphosphate was terminated after the tenth increment.

Example 3

A solution containing 92 grams per liter sodium tripolyphosphate in distilled water was added to a General Electric GSD-950-01 dishwasher in which was circulating 8 liters of the water of the same hardness as used in Example 2, to which had been added 8 grams of Carnation Instant Nonfat Dry Milk. Calculations based on information in the U.S.D.A. Agricultural Handbook No. 8 (1975) indicate that 8 grams of instant nonfat dry milk contain 3.05 millimoles of combined calcium and magnesium. Total hardness present was 9.3 millimoles (from the water)+3.05 millimoles (from the milk), or a total of 12.4 millimoles. The temperature of the circulating water was 53.9°. Because it was known, the water was harder than in Example 2, the $Na_5P_3O_{19}$ was added in 10 ml. increments, with the voltage drop across a 464 delta resistor recorded after the third increment, 10 seconds after each incremental addition.

| Increment | Millimoles $Na_5P_3O_{10}$ Present | Voltage Drop | Delta Voltage Drop |
|---|---|---|---|
| 0 | 0.00 | 3.070 | 0 |
| — | — | — | — |
| 3 | 7.50 | 3.306 | — |
| 4 | 10.00 | 3.422 | .116 |
| 5 | 12.50 | 3.542 | .120 |
| 6 | 15.00 | 3.646 | .104 |
| 7 | 17.50 | 3.741 | .095 |

Control logic correctly interpreted the fifth increment as the end-point, demonstrating that the additional hardness originating from the soil load was detected.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sequestration method for sequestering the calcium and magnesium hardness elements in a wash water solution containing such hardness, comprising the steps of:
   (a) adding sodium tripolyphosphate to said wash water solution at a preselected rate slow enough to permit the determination of the effect upon the conductivity of said wash water solution of incremental amounts of said sodium tripolyphosphate;
   (b) periodically sensing, at time intervals which are constant relative to the rate of addition of said sodium tripolyphosphate, the electrical conductivity of said wash water solution to obtain thereby a plurality of conductivity values;
   (c) determining a plurality of rates of change in said conductivity from said plurality of conductivity values;
   (d) detecting from said plurality of rates of change the substantially maximum rate of change of said conductivity values which occurs approximately when a 1:1 molar ratio of hardness elements to sodium tripolyphosphate is reached; and
   (e) terminating the addition of sodium tripolyphosphate to said wash water solution when said substantially maximum rate of change of said conductivity values is detected.

2. The method as claimed in claim 1, wherein said sodium tripolyphosphate is added to said wash water solution independently of any detergent added to said wash water solution.

3. The method as claimed in claim 1, wherein said sodium tripolyphosphate is added as a component of a detergent composition.

4. The method as claimed in claim 1, wherein in step (a), the rate of addition is constant, in step (b), the sensing of the electrical conductivity occurs at substantially equally spaced time intervals; in step (c), said rate of change of conductivity values is determined from time adjacent conductivity values; and in step (e), said addition is terminated when three successive rates of change of conductivity values are determined in step (d) to be lesser than the immediately preceding rate of change of conductivity value.

5. The method as claimed in claim 4, wherein steps (b) and (b) comprise:
   (1) sensing the electrical conductivity of said wash water solution to obtain a first conductivity value;
   (2) sensing said electrical conductivity of said wash water solution after the lapse of a preselected interval of time from step (1) to obtain a second conductivity value;
   (3) sensing said electrical conductivity of said wash water solution after the lapse of said preselected interval of time from step (2) to obtain a third conductivity value;
   (4) sensing said electrical conductivity of said wash water solution after the lapse of said preselected interval of time from step (3) to obtain a fourth conductivity value;
   (5) sensing said electrical conductivity of said wash water solution after the lapse of said preselected interval of time from step (4) to obtain a fifth conductivity value;
   (6) subtracting said first conductivity value from said second conductivity value to obtain a first rate of change in conductivity value;
   (7) subtracting said second conductivity value from said third conductivity value to obtain a second rate of change of conductivity value;
   (8) subtracting said third conductivity value from said fourth conductivity value to obtain a third rate of change of conductivity value; and
   (9) subtracting said fourth conductivity value from said fifth conductivity value to obtain a fourth rate of change of conductivity value, and wherein step (d) comprises the steps of:
   (i) discarding said first conductivity value, substituting said second conductivity value as said first conductivity value, substituting said third conductivity value as said second conductivity value, substituting said fourth conductivity value as said third conductivity value, and substituting said fifth conductivity value as said fourth conductivity value; and
   (ii) repeating sequentially steps (5)–(9) until said first rate of change of conductivity value is greater than both said second rate of change of conductivity value, said third rate of change of conductivity value and said fourth rate of change of conductivity value.

6. The method as claimed in claim 4, wherein said sodium tripolyphosphate is added to said wash water solution independently of any detergent added to said wash water solution.

7. The method as claimed in claim 4, wherein said sodium tripolyphosphate is a component of detergent added to said wash water solution.

8. A method for eliminating the calcium and magnesium hardness elements in a wash water solution containing such hardness, comprising steps of:
   (a) adding said sodium tripolyphosphate to said wash water solution at a preselected rate slow enough to permit the determination of the effect upon the conductivity of said wash water solution of incremental amounts of said sodium tripolyphosphate;
   (b) periodically sensing the electrical conductivity of said wash water solution;
   (c) detecting a first substantial rise in said conductivity of said wash water solution above an initial conductivity;
   (d) adding a base to raise the pH of said wash water solution to at least 11 prior to step (a) or subsequent to step (c); and
   (e) adding 1.5 times the amount of sodium tripolyphosphate which was added before said first substantial rise in said conductivity occurred, thereby achieving an approximate 1:1 molar ratio of calcium hardness, calculated as $CaCO_3$, to sodium tripolyphosphate, whereby calcium hardness is eliminated by sequestration; magnesium hardness is eliminated by precipitation.

9. The method as claimed in claim 8, wherein sodium tripolyphosphate is added to said wash water solution independently of any detergent added to said wash water solution.

10. The method as claimed in claim 8, wherein the initial time period during which said sodium tripolyphosphate is added to said wash water until said first substantial rise in conductivity occurs is measured, and wherein the addition of said sodium tripolyphosphate is thereafter continued at the same preselected rate for a period of time which is 1.5 times as long as said initial time period.

11. The method as claimed in claim 8, wherein the initial time period during which said sodium tripolyphosphate is added to said wash water until said first substantial rise in conductivity occurs is measured, and wherein the addition of said sodium tripolyphosphate is thereafter continued at a second preselected rate which differs from the initial preselected rate for a period of time which adds 1.5 times more than the initial amount of sodium tripolyphosphate which was added to the wash water solution.

12. Apparatus adapted for sequestering the calcium and magnesium hardness elements in a wash water solution containing such hardness elements, which comprises:
   (a) means for generating a conductivity signal in accordance with the electrical conductivity of said wash water solution;
   (b) first means responsive to said conductivity signal for detecting a maximum rate of change of said electrical conductivity, and for supplying a dispensing signal until said maximum rate of change is detected; and
   (c) means for dispensing, in response to said dispensing signal, sodium tripolyphosphate to said wash water solution, whereby the dispensing of said sodium tripolyphosphate into said wash water solution is terminated when said maximum rate of change is detected.

13. The apparatus as claimed in claim 12, wherein said means for providing a conductivity signal comprises:
   means for supplying an A.C. signal;
   means responsive to said A.C. signal for providing a voltage signal having an amplitude in accordance with said electrical conductivity; and
   analog to digital converter means responsive to said voltage signal for producing said conductivity signal in accordance with said voltage signal.

14. The apparatus as recited in claim 13, wherein said voltage signal comprises:
   a first conductivity electrode disposed in said solution and connected to said A.C. signal means;
   a second conductivity electrode disposed in said solution; and
   resistor means having a first side connected to said A.C. signal means for providing said voltage signal, and having a second side connected to said second conductivity electrode.

15. The apparatus as claimed in claim 12, wherein said first means comprises:
   means responsive to said conductivity signal for determining a plurality of rates of change of said electrical conductivity; and
   means responsive to said plurality of rates of change of said electrical conductivity for detecting from said plurality of rates of change said maximum rate of change of said electrical conductivity.

16. The apparatus as claimed in claim 15, wherein said means for detecting from said plurality of rates of change said maximum rate of change comprises means for indicating said maximum rate of change when at least two successive rates of change of said conductivity are less than the immediately preceding rate of change of said electrical conductivity.

17. The apparatus as recited in claim 12, wherein said first means comprises:
   processor means under stored program control having an input port responsive to said conductivity signal and an output port; and
   means responsive to said output port for supplying said dispensing signal.

18. Apparatus adapted for eliminating the calcium and magnesium hardness elements in a wash water solution containing such hardness elements, which comprises:
   (a) means for generating a conductivity signal in accordance with electrical conductivity of said wash water solution;
   (b) means for supplying a dispensing signal;
   (c) means for dispensing, in response to said dispensing signal, sodium tripolyphosphate to said wash water solution;
   (d) first means responsive to said conductivity signal for detecting a first substantial rise of said electrical conductivity from an initial electrical conductivity, and for continuing said dispensing signal until 1.5 times the amount of sodium tripolyphosphate which was added before said substantial rise of said electrical conductivity has been added to said wash water solution, thereby achieving an approximate 1:1 molar ratio of calcium hardness, calculated $CaCO_3$, to sodium tripolyphosphate, whereby calcium hardness is eliminated by sequestration; and
   (e) means for adding a base to raise the pH of said wash water solution to at least 11 either (i) prior to detecting said initial conductivity or (ii) subsequent to detecting said first rise of said electrical conductivity, whereby magnesium hardness is eliminated by precipitation.

19. The apparatus as claimed in claim 18, wherein said means for providing a conductivity signal comprises:
   means for supplying an A.C. signal;
   means responsive to said A.C. signal for providing a voltage signal having an amplitude in accordance with said electrical conductivity; and
   analog to digital converter means responsive to said voltage signal for producing said conductivity signal in accordance with said voltage signal.

20. The apparatus as recited in claim 19, wherein said voltage signal comprises:
   a first conductivity electrode disposed in said solution and connected to said A.C. signal means;
   a second conductivity electrode disposed in said solution; and
   resistor means having a first side connected to said A.C. signal means for providing said voltage signal, and having a second side connected to said second conductivity electrode.

21. The apparatus as claimed in claim 18, wherein said first means comprises:
   means responsive to said conductivity signal for determining said initial electrical conductivity of said wash water solution;
   means responsive to said conductivity signal for detecting said first substantial rise by an increase in said electrical conductivity above said initial electrical conductivity which at least equals a predetermined magnitude; and
   means for producing said dispensing signal until 1.5 times the amount of sodium tripolyphosphate which was added before said substantial rise of said electrical conductivity has been added to said wash water solution.

22. The apparatus as claimed in claim 21, wherein said means for dispensing sodium tripolyphosphate comprises means for dispensing, in response to said dispensing signal, sodium tripolyphosphate to said wash water solution at a substantially constant rate, and
   wherein said means for producing said dispensing signal comprises register means for measuring the amount of time said sodium tripolyphosphate is dispensed to said wash water solution until said first substantial rise of said electrical conductivity is detected, and timer means for providing said dispensing signal after detection of said first substantial rise for a time period substantially equal to 1.5 times the amount of time measured by said register means.

23. The apparatus as recited in claim 18 wherein said first means comprises:
   processor means under stored program control having an input port responsive to said conductivity signal and an output port; and
   means responsive to said output port for supplying said dispensing signal.

24. The apparatus as claimed in claim 21 wherein said predetermined magnitude is at least 80 $\mu$mhos.

* * * * *